(12) United States Patent
Fenlon et al.

(10) Patent No.: US 10,369,293 B2
(45) Date of Patent: Aug. 6, 2019

(54) MEDICAMENT DELIVERY DEVICE WITH TRIGGER BUTTON

(71) Applicant: SANOFI-AVENTIS DEUTSCHLAND GMBH, Frankfurt am Main (DE)

(72) Inventors: Derek Fenlon, Wexford (IE); Pascal Launois, Dublin (IE); Julian McDonnell, Co. Wicklow (IE); Martina Moyne, Co. Donegal (IE); Conor Mulcahy, Co. Dublin (IE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 850 days.

(21) Appl. No.: 14/433,315

(22) PCT Filed: Oct. 1, 2013

(86) PCT No.: PCT/EP2013/070460
§ 371 (c)(1),
(2) Date: Apr. 2, 2015

(87) PCT Pub. No.: WO2014/053494
PCT Pub. Date: Apr. 10, 2014

(65) Prior Publication Data
US 2015/0246180 A1 Sep. 3, 2015

(30) Foreign Application Priority Data
Oct. 4, 2012 (EP) ..................... 12187311

(51) Int. Cl.
A61M 5/315 (2006.01)
A61M 5/20 (2006.01)
(Continued)

(52) U.S. Cl.
CPC ............ A61M 5/3158 (2013.01); A61M 5/20 (2013.01); A61M 5/3135 (2013.01);
(Continued)

(58) Field of Classification Search
CPC ........ A61M 5/3135; A61M 5/20; A61M 5/30; A61M 5/3202; A61M 5/24; A61M 5/3158;
(Continued)

(56) References Cited

U.S. PATENT DOCUMENTS 4,349,712 A * 9/1982 Michalski ............ H01H 13/702
200/5 A
5,503,628 A * 4/1996 Fetters ................ A61M 5/2033
222/325

(Continued)

FOREIGN PATENT DOCUMENTS

CN 101485559 7/2009
CN 101505816 8/2009
(Continued)

OTHER PUBLICATIONS

Bittner et al, "TASK1 modulates inflammation and neurodegeneration in autoimmune inflammation of the central nervous system," Brain: A Journal of Neurology, 132:2501-2516 (2009).
(Continued)

Primary Examiner — Imani N Hayman
Assistant Examiner — Tiffany Legette
(74) Attorney, Agent, or Firm — Fish & Richardson P.C.

(57) ABSTRACT

Described is a medicament delivery device (1) comprising a case (2) adapted to hold a container (3) of a medicament, a drive mechanism (5) adapted to expel the medicament from the container (3), and a trigger button (6) disposed on the case (2) and operably coupled to the drive mechanism (5). The trigger button (6) has a concave position and a convex position. Movement of the trigger button (6) from the convex position to the concave position causes activation of the drive mechanism (5).

18 Claims, 2 Drawing Sheets

(51) Int. Cl.
*A61M 5/31* (2006.01)
*A61M 5/32* (2006.01)
*A61M 5/24* (2006.01)
*A61M 5/30* (2006.01)

(52) U.S. Cl.
CPC ............. *A61M 5/3202* (2013.01); *A61M 5/24* (2013.01); *A61M 5/30* (2013.01); *A61M 2205/582* (2013.01); *A61M 2205/583* (2013.01)

(58) Field of Classification Search
CPC .. A61M 5/32; A61M 5/315; A61M 2205/583; A61M 2205/582; A51M 5/20; A51M 5/24; A51M 5/3135; A51M 5/3158; A51M 5/3202; A51M 5/3287; A51M 5/422
USPC .................................................... 604/192, 67
See application file for complete search history.

(56) References Cited

U.S. PATENT DOCUMENTS

| | | | | |
|---|---|---|---|---|
| 2004/0054319 | A1* | 3/2004 | Langley | A61M 5/14244 604/67 |
| 2006/0200111 | A1* | 9/2006 | Moehle | A61M 25/0009 604/539 |
| 2007/0197968 | A1* | 8/2007 | Pongpairochana | A61M 5/20 604/131 |
| 2008/0033393 | A1* | 2/2008 | Edwards | A61M 5/2033 604/503 |
| 2008/0296141 | A1* | 12/2008 | Ogatsu | H01H 13/705 200/535 |
| 2011/0118662 | A1* | 5/2011 | Mhatre | A61M 5/1413 604/67 |
| 2011/0301534 | A1* | 12/2011 | Renz | A61M 5/2066 604/82 |
| 2012/0078180 | A1 | 3/2012 | Fujioka et al. | |
| 2012/0165747 | A1 | 6/2012 | Lanin et al. | |

FOREIGN PATENT DOCUMENTS

| | | |
|---|---|---|
| CN | 102065935 | 5/2011 |
| EP | 2301468 | 3/2011 |
| EP | 2361647 | 8/2011 |
| GB | 2461088 | 12/2009 |
| JP | S60-10322 | 1/1985 |
| JP | S63-82327 | 4/1988 |
| JP | H07-261864 | 10/1995 |
| WO | WO 2011/010467 | 1/2011 |
| WO | 2011/095486 | 8/2011 |
| WO | WO 2011/101381 | 8/2011 |
| WO | 2012/072559 | 6/2012 |
| WO | 2012/072562 | 6/2012 |
| WO | 2012/072563 | 6/2012 |

OTHER PUBLICATIONS

European Search Report issued in EP12187308 dated Mar. 18, 2013 (6 pages).
International Search Report and Written Opinion issued in PCT/EP2013/070463 dated Jan. 14, 2014 (9 pages).
Japanese Office Action in Application No. 2015-534988, dated Aug. 1, 2017,7 pages.
Chinese Office Action in Application No. 201380060937.1, dated Jun. 16, 2017, 17 pages (with English Translation).
Chinese Office Action in Application No. 201380060937.1, dated Nov. 4, 2016, 17pages (with English Translation).
International Preliminary Report on Patentability in International Application No. PCT/EP2013/070460, dated Apr. 7, 2015, 6 pages.
International Search Report and Written Opinion in International Application No. PCT/EP2013/070460, dated Nov. 20, 2013, 9 pages.

* cited by examiner

MEDICAMENT DELIVERY DEVICE WITH TRIGGER BUTTON

This application is a 371 U.S. National Application of PCT/EP2013/070460, filed on Oct. 1, 2013, which claims priority to European Patent Application Nos. 12187311.1, filed on Oct. 4, 2012, the entire contents of which are incorporated herein by reference.

TECHNICAL FIELD

The invention relates to a medicament delivery device with a trigger button.

BACKGROUND OF THE INVENTION

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Conventional delivery devices may also have limited feedback mechanisms. For example, some conventional delivery devices may only provide an audible feedback when an injection is initiated.

Thus, there remains a need for an improved medicament delivery device with a trigger button.

SUMMARY OF THE INVENTION

It is accordingly an object of the present invention to provide an improved medicament delivery device with a trigger button.

In an exemplary embodiment, a medicament delivery device according to the present invention comprises a case adapted to hold a container of a medicament, a drive mechanism adapted to expel the medicament from the container, and a trigger button disposed on the case and operably coupled to the drive mechanism. The trigger button has a concave position and a convex position. Movement of the trigger button from the convex position to the concave position causes activation of the drive mechanism.

In an exemplary embodiment, the container includes a needle. The container is slidably disposed in the case and moves between a first position in which the needle is substantially covered by the case and a second position in which the needle extends beyond a distal end of the case.

In an exemplary embodiment, the drive mechanism includes a plunger adapted to apply a force on a stopper in the container and a drive spring adapted to apply a force on the plunger.

In an exemplary embodiment, the trigger button is disposed on a proximal end of the case.

In an exemplary embodiment, the trigger button is made from at least one flexible thermoelastic polymer. The at least one flexible thermoelastic polymer includes a styrenic block copolymer, a polyolefin blend, an elastomeric alloy, thermoplastic polyurethane, thermoplastic copolyester or a thermoplastic polyamide. The trigger button creates a hermetic seal for a proximal end of the case.

In an exemplary embodiment, a diameter of the trigger button is substantially equal to a diameter of the case.

In an exemplary embodiment, the medicament delivery device further comprises an interlock member telescopically coupled to the case and translatable between an extended position relative to the case and a retracted position relative to the case. The interlock member is operably coupled to the trigger button. Translation of the interlock member from the extended position to the retracted position causes transition of the trigger button from the concave position to the convex position. The interlock member is biased in the extended position. The interlock member is locked in the extended position after the interlock member translates from the retracted position to the extended position and the trigger button transitions from the convex position to the concave position.

In an exemplary embodiment, an audible feedback is generated when the trigger button transitions from the concave position to the convex position.

In an exemplary embodiment, the trigger button is biased in the concave position.

The exemplary embodiments of the medicament delivery device according to the present invention provide a visually uncluttered design and has the appearance of less components. The exemplary embodiments of the medicament delivery device provide the user with a potential positive, but soft feel when depressing the trigger button.

The exemplary embodiments of the trigger button according to the present invention may return a visual and/or tactile feedback of the sequencing of mechanisms for displacing a medicament from a container in the delivery device.

The exemplary embodiments of the trigger button according to the present invention may remove a potential pinch point (e.g., skin from a hand being caught between a conventional button and an outer housing of the delivery device when the button is pressed) from the medicament delivery device.

The exemplary embodiments of the trigger button according to the present invention may provide a visual and/or tactile orientation control for the user thus reducing the risk of positioning a needle-end of the delivery device against a thumb.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
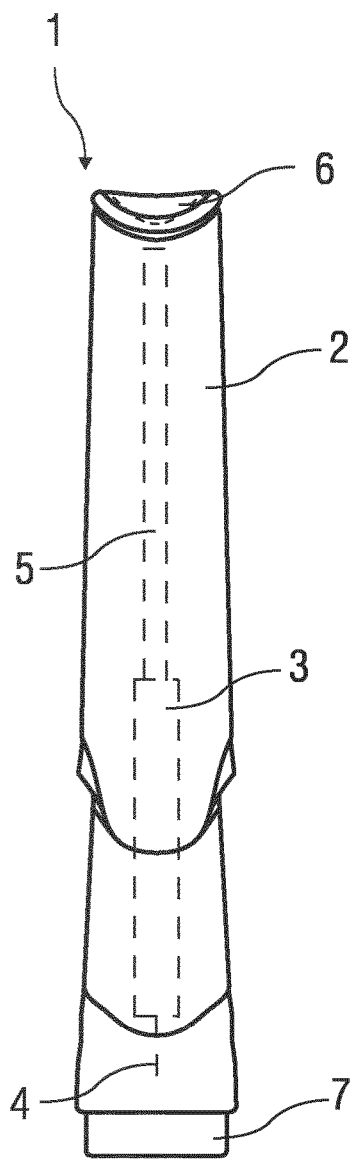
FIG. 1 is a lateral view of an exemplary embodiment of a medicament delivery device with an interlock member in an extended position.
Figure 2:
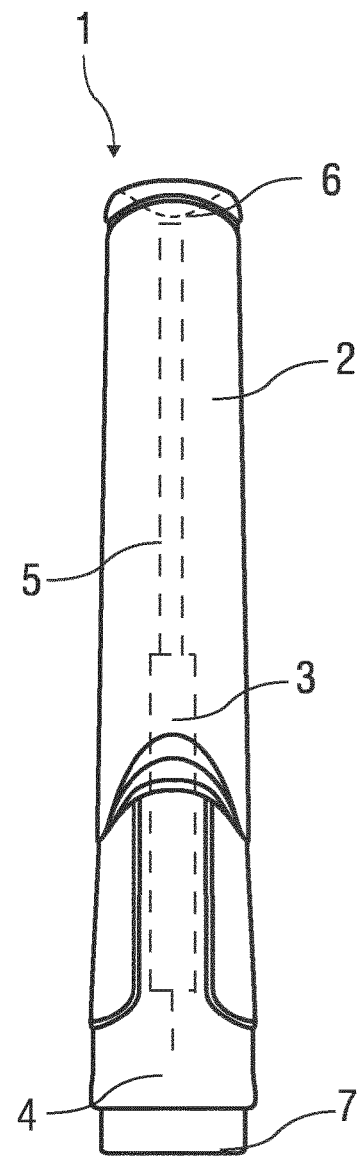
FIG. 2 is another lateral view of an exemplary embodiment of a medicament delivery device with an interlock member in an extended position.

FIGS. 1 and 2 show an exemplary embodiment of a medicament delivery device 1 (e.g., an autoinjector, a pen injector, etc.). In the exemplary embodiment, the delivery device 1 comprises a case 2 adapted to hold a container 3 (e.g., a cartridge, a syringe) with a needle 4 removably coupled to the container 3 or integrally formed therewith. The delivery device 1 includes comprises a drive mechanism 5 for displacing the medicament from the container 3 through the needle 4. In an exemplary embodiment, the drive mechanism 5 may include a plunger and a drive spring which, when activated, exerts a force on the plunger to push a stopper in the container 3 to expel the medicament.

In an exemplary embodiment, the delivery device 1 includes a trigger button 6 for actuating the drive mechanism 5. The trigger button 6 may be disposed on a proximal end of the case 2. In other exemplary embodiments, the trigger button 6 may be disposed on a side of the case 2. In an exemplary embodiment, the trigger button 6 is made from at least one flexible thermoplastic elastomer, e.g. a styrenic block copolymer, a polyolefin blend, an elastomeric alloy, thermoplastic polyurethane, thermoplastic copolyester or a thermoplastic polyamide. The trigger button 6 may be coupled to the case 2 to create a substantially hermetic seal. Further, a diameter of the trigger button 6 may correspond to a diameter of the case 2.

In an exemplary embodiment, the trigger button 6 may have a concave position and a convex position. In an exemplary embodiment, the trigger button 6 may be biased (e.g., via its elastic properties) in either position.

In an exemplary embodiment, an interlock member 7 (e.g., a sleeve) is telescopically coupled to the case 2 and operably coupled to the trigger button 6. The interlock member 7 may be biased in an extended position (FIGS. 1 and 2) relative to the case 2 by, for example, a spring (not shown).

As shown in the exemplary embodiments in FIG. 1 and FIG. 2, the trigger button 6 is in a concave position prior to use of the delivery device 1. Those of skill in the art will understand that the trigger button 6 may be in a convex position prior to use of the delivery device 1. The interlock member 7 is in the extended position. In an exemplary embodiment, the container 3 may be slidably arranged in the case 2 between a retracted position in which the needle 4 is covered by the case 2 and an extended position in which the needle 4 is exposed (e.g., for penetration of an injection site). If the container 3 is slidably arranged in the case 2, the container 3 would be in the retracted position prior to use.

If the container 3 is fixedly arranged in the case 2, the needle 4 may be covered by the interlock member 7 extending beyond a distal end of the case 2.

Figure 3:
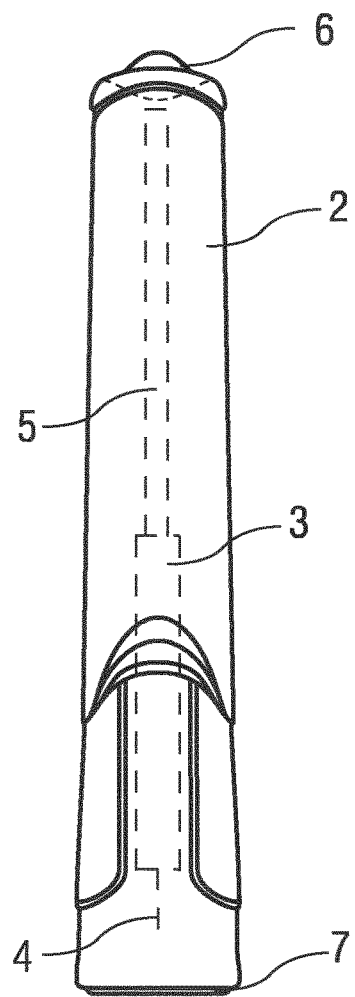
FIG. 3 is a lateral view of an exemplary embodiment of a medicament delivery device an interlock member in a retracted position.
Figure 4:
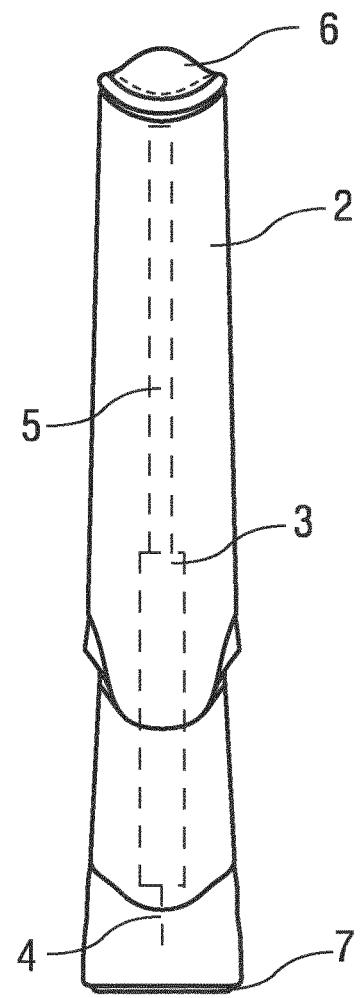
FIG. 4 is another lateral view of an exemplary embodiment of a medicament delivery device with an interlock member in a retracted position.

As shown in the exemplary embodiments in FIGS. 3 and 4, when the delivery device 1 is placed on an injection site, the interlock member 7 translates from the extended position to the retracted position. When the interlock member 7 is in the retracted position, the trigger button 6 achieves a convex position. In another exemplary embodiment, the trigger button 6 may transition to the convex position as the interlock member 7 is retracted relative to the case 2. If the delivery device 1 is removed from the injection site (e.g., for realignment), the trigger button 6 may return to the concave position (e.g., under a biasing force). When the trigger button 6 is in the convex position, it provides a visual feedback to a user that the delivery device 1 may be actuated. When the trigger button 6 transitions from the concave position to the convex position, an audible feedback (e.g., a "pop" noise) may be provided due to the elastic properties of the trigger button 6.

When the trigger button 6 is pressed, it may actuate the drive mechanism 5 to advance the container 3 for insertion of the needle 4 into the injection site and advance the plunger into the container 3 to expel the medicament. In another exemplary embodiment, actuation of the drive mechanism may only advance the plunger into the container 3 to expel the medicament.

When the delivery device 1 is removed from the injection site, the interlock member 7 may return to the extended position under the biasing force of the spring, and the trigger button 6 may return to the concave position. In an exemplary embodiment, after the trigger button 6 has been pressed 6 it may disengage the interlock member 7, such that if the delivery device 1 is pressed against the injection site, even if the interlock member 7 translates to the retracted position, the trigger button 6 remains in the concave position. In an exemplary embodiment, the interlock member 7 is locked in the extended position after the delivery device 1 is removed from the injection site.

While the exemplary embodiments show the trigger button 6 having a circular cross-section, those of skill in the art will understand that the trigger button 6 may be square, rectangular, elliptical or any other shape.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device comprising:
a container of a medicament, the container including a needle;
a case adapted to hold the container, wherein the container is slidably disposed in the case and moves between a first position in which the needle is substantially covered by the case and a second position in which the needle extends beyond a distal end of the case;
a drive mechanism adapted to expel the medicament from the container;
a trigger button disposed on the case and operably coupled to the drive mechanism, the trigger button having a concave position and a convex position, wherein movement of the trigger button between the convex position and the concave position causes activation of the drive mechanism; and an interlock member telescopically coupled to the case and translatable between an extended position relative to the case and a retracted position relative to the case, wherein the interlock member is operably coupled to the trigger button.

2. The medicament delivery device according to claim 1, wherein the drive mechanism includes a plunger adapted to apply a force on a stopper in the container and a drive spring adapted to apply a force on the plunger.

3. The medicament delivery device according to claim 1, wherein a diameter of the trigger button is substantially equal to a diameter of the case.

4. The medicament delivery device according to claim 1, wherein translation of the interlock member from the extended position to the retracted position causes transition of the trigger button from the concave position to the convex position.

5. The medicament delivery device according to claim 1, wherein the interlock member is biased in the extended position.

6. The medicament delivery device according to claim 1, wherein the interlock member is locked in the extended position after the interlock member translates from the retracted position to the extended position and the trigger button transitions from the convex position to the concave position.

7. The medicament delivery device according to claim 1, wherein an audible feedback is generated when the trigger button transitions from the concave position to the convex position.

8. The medicament delivery device according to claim 1, wherein the trigger button is biased in the concave position.

9. The medicament delivery device according to claim 1, wherein the trigger button is disposed on a proximal end of the case.

10. The medicament delivery device of claim 9, wherein the trigger button is disposed on a proximal-most end of the case.

11. The medicament delivery device according to claim 1, wherein the trigger button is made from at least one flexible thermoelastic polymer.

12. The medicament delivery device according to claim 11, wherein the at least one flexible thermoelastic polymer includes a styrenic block copolymer, a polyolefin blend, an elastomeric alloy, thermoplastic polyurethane, thermoplastic copolyester or a thermoplastic polyamide.

13. The medicament delivery device according to claim 11, wherein the trigger button creates a hermetic seal for a proximal end of the case.

14. A medicament delivery device comprising:

a case adapted to hold a container of a medicament;

a trigger button disposed on the case, the trigger button having a convex position and a concave position, the trigger button configured to move between the convex position and the concave position;

a drive mechanism operably coupled to the trigger button, the drive mechanism configured to expel the medicament from the container in response to the trigger button moving between the convex position and the concave position; and an interlock member telescopically coupled to the case and translatable between an extended position relative to the case and a retracted position relative to the case, wherein the interlock member is operably coupled to the trigger button.

15. The medicament delivery device according to claim 14, wherein the trigger button is biased in the concave position.

16. The medicament delivery device according to claim 14, wherein the trigger button has elastic properties that produce an audible feedback in response to the trigger button moving between the convex position and the concave position.

17. The medicament delivery device of claim 14, wherein the trigger button is disposed on a proximal-most end of the case.

18. A medicament delivery device comprising:

a case adapted to hold a container of a medicament;

a drive mechanism adapted to expel the medicament from the container, wherein the drive mechanism includes a plunger adapted to apply a force on a stopper in the container and a drive spring adapted to apply a force on the plunger;

a trigger button disposed on the case and operably coupled to the drive mechanism, the trigger button having a concave position and a convex position, wherein movement of the trigger button between the convex position and the concave position causes activation of the drive mechanism; and an interlock member telescopically coupled to the case and translatable between an extended position relative to the case and a retracted position relative to the case, wherein the interlock member is operably coupled to the trigger button.

* * * * *